(12) United States Patent
Laughlin

(10) Patent No.: US 9,023,829 B2
(45) Date of Patent: *May 5, 2015

(54) METHOD OF REGULATING NFATC2 ACTIVITY IN LYMPHOCYTES

(75) Inventor: Mary J. Laughlin, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/047,295

(22) Filed: Mar. 14, 2011

(65) Prior Publication Data

US 2012/0022130 A1 Jan. 26, 2012

Related U.S. Application Data

(60) Provisional application No. 61/313,361, filed on Mar. 12, 2010.

(51) Int. Cl.
| | |
|---|---|
| *A01N 43/04* | (2006.01) |
| *A61K 31/7105* | (2006.01) |
| *C12N 5/0783* | (2010.01) |
| *A61K 35/12* | (2006.01) |

(52) U.S. Cl.
CPC ....... *A61K 31/7105* (2013.01); *A61K 2035/124* (2013.01); *C12N 5/0636* (2013.01); *C12N 2501/65* (2013.01)

(58) Field of Classification Search
None
See application file for complete search history.

(56) References Cited

U.S. PATENT DOCUMENTS

2005/0191283 A1* 9/2005 Kadereit et al. ........... 424/93.21
2008/0227689 A1* 9/2008 Marth et al. ..................... 514/2

OTHER PUBLICATIONS

Griffiths-Jones, Sam. (2004) The microRNA Registry, Nucleic Acids Research, v.32:D109-D111.*
Weitzel, et al. (2009) microRNA 184 regulates expression of NFATc2 in umbilical cord blood CD4+ T cells. Blood, v.113(26):6648-57.*

* cited by examiner

*Primary Examiner* — Jennifer McDonald
(74) *Attorney, Agent, or Firm* — Tarolli, Sundheim, Covell & Tummino LLP

(57) ABSTRACT

A method of decreasing NFATc2 activity in a lymphocyte includes administering to the lymphocyte an amount of an NFATc2 mRNA antagonist that binds to a binding site on the 3'UTR of NFATc2 mRNA effective to decrease the activity of NFATc2 mRNA in the lymphocyte.

17 Claims, 5 Drawing Sheets

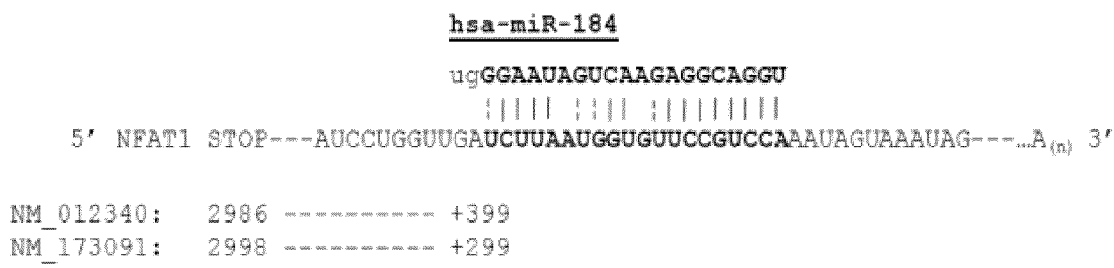
Fig. 3
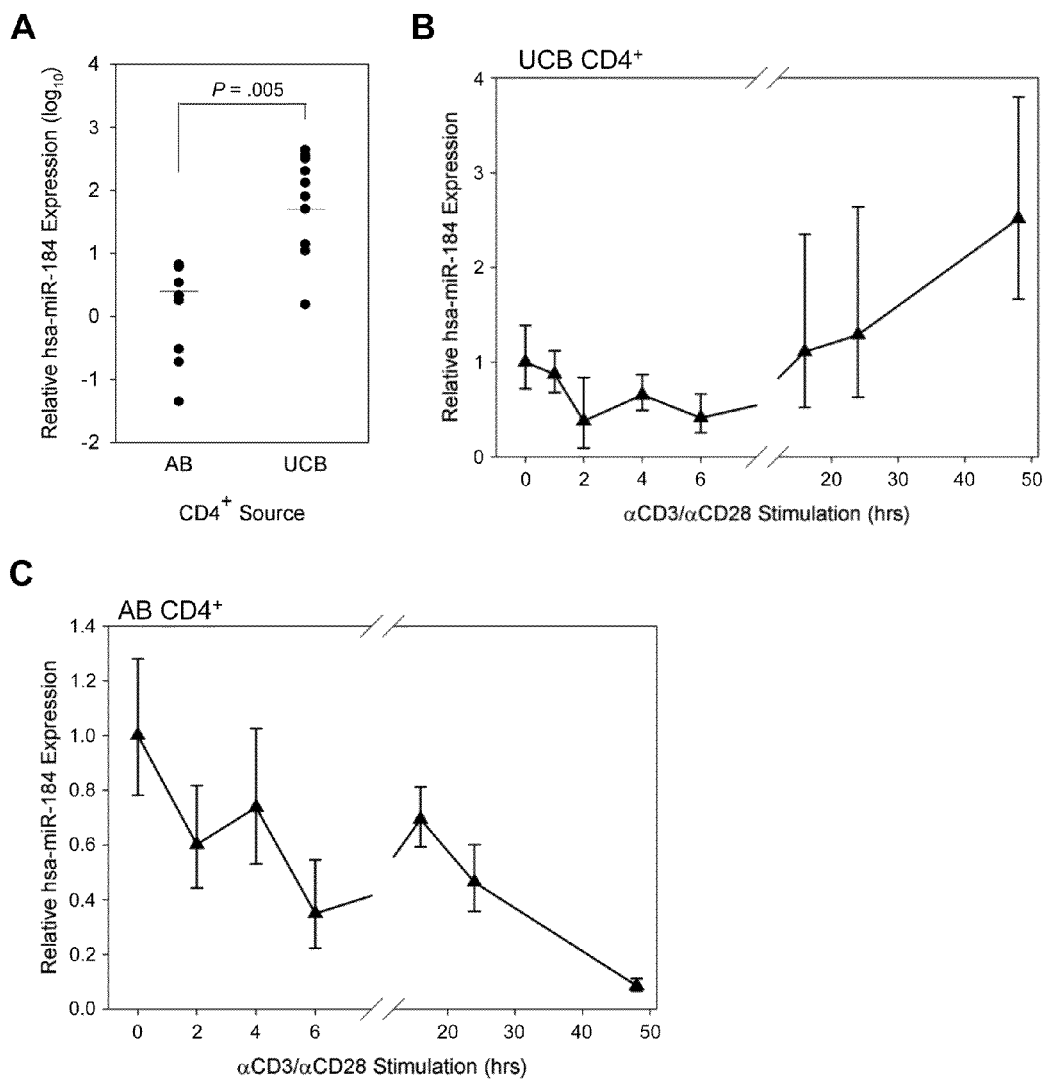
Figs. 4A-C

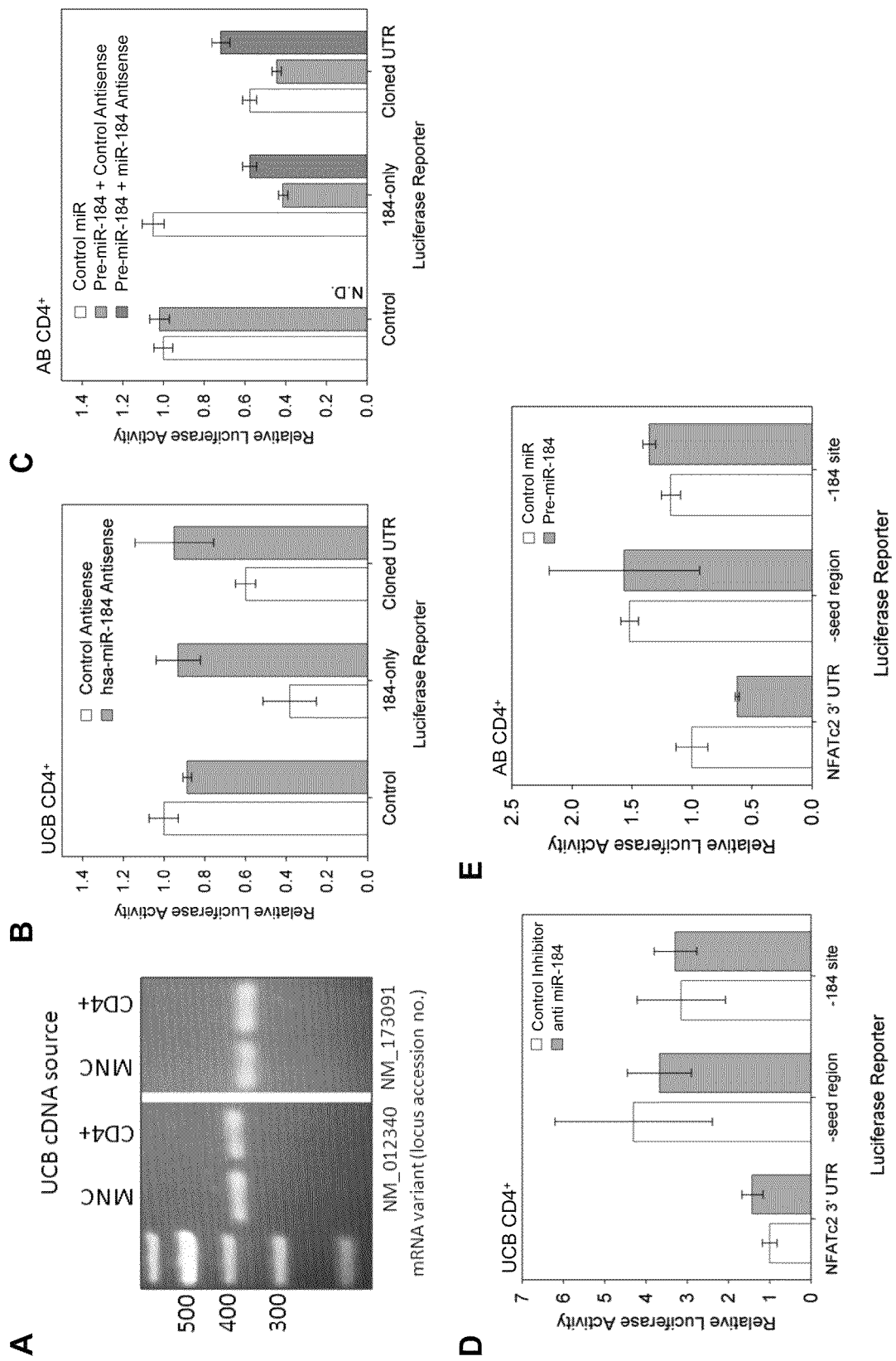
Figs. 5A-E

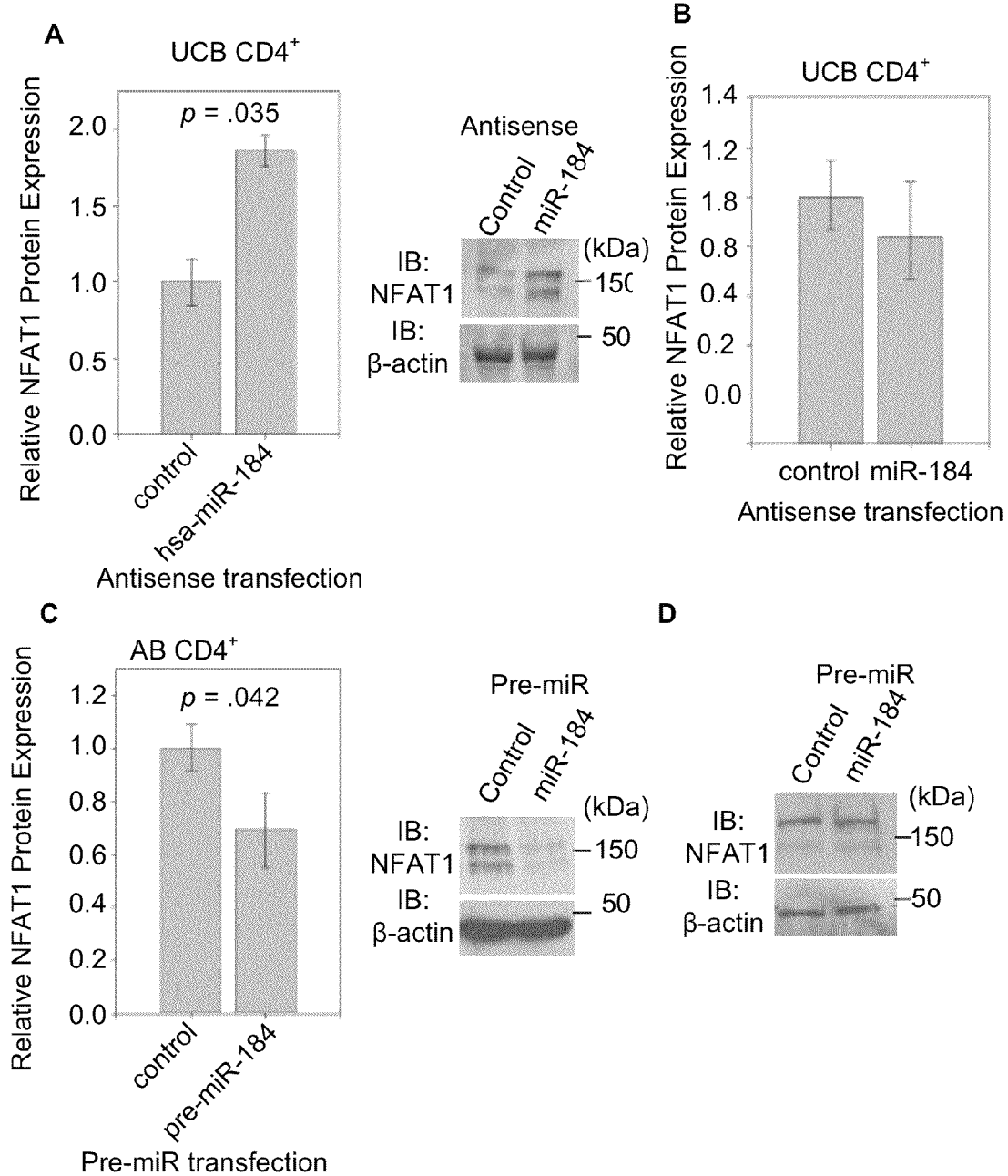
Figs. 6A-D

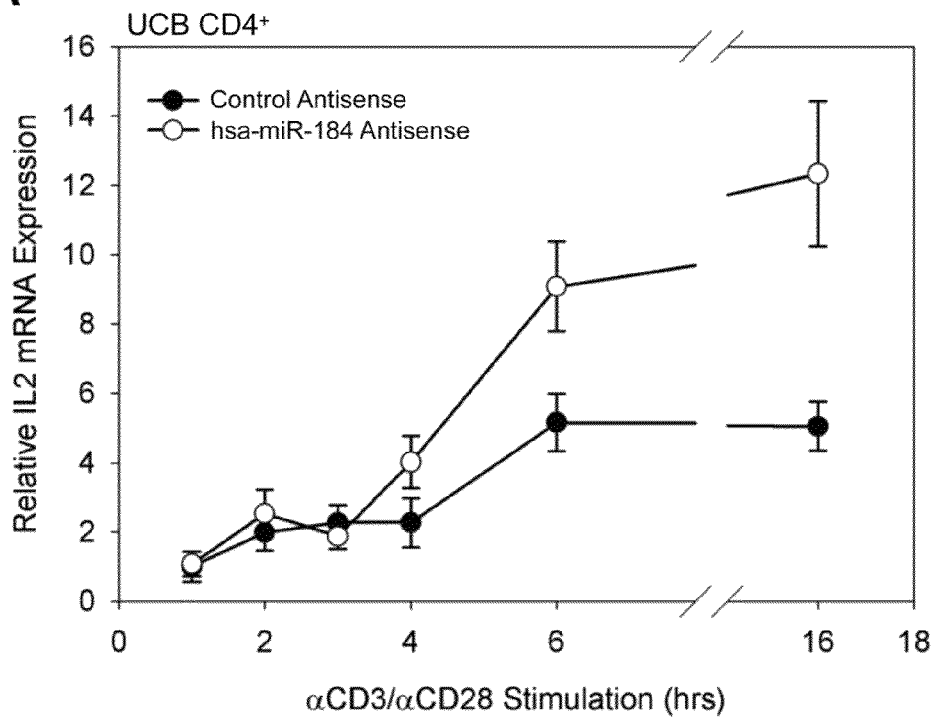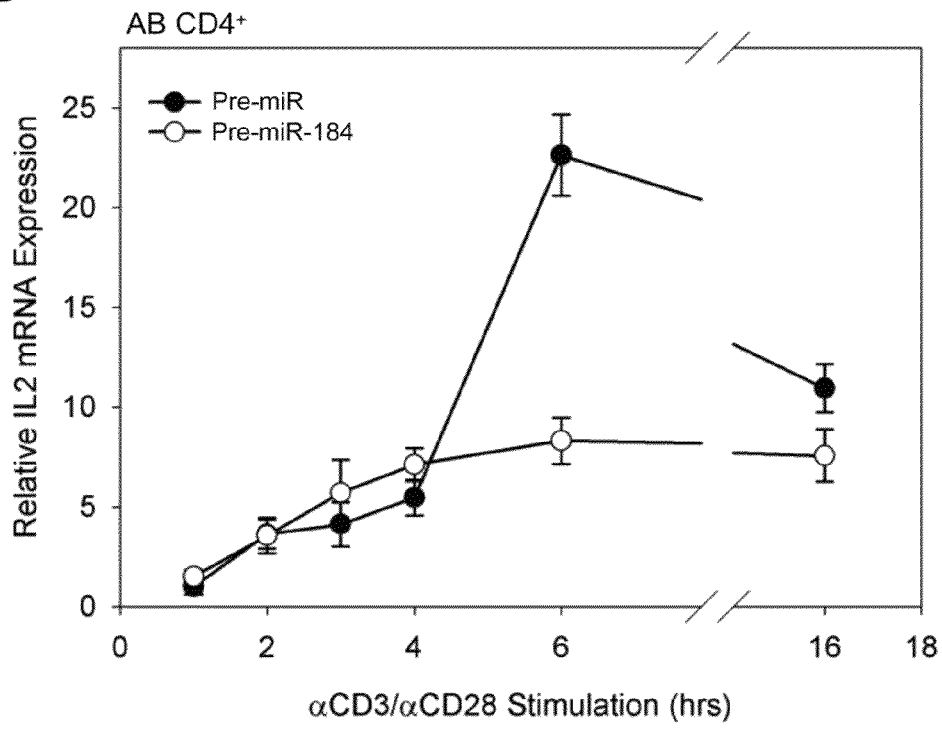
Figs. 7A-B

METHOD OF REGULATING NFATC2 ACTIVITY IN LYMPHOCYTES

RELATED APPLICATION

This application claims priority from U.S. Provisional Application No. 61/313,361, filed Mar. 12, 2010, the subject matter of which is incorporated herein by reference in its entirety.

TECHNICAL FIELD

The present invention generally relates to methods of decreasing NFATc2 expression in lymphocytes and to methods of treating T-cell mediated disorders.

BACKGROUND

Numerous reports spanning two decades have confirmed umbilical cord blood (UCB) as a clinical source of hematopoietic progenitors for allogeneic transplantation in the treatment of hematologic malignancies. Despite the primary drawback of slower kinetics of myeloid engraftment as a result of limited graft cell dose, UCB has several advantages over bone marrow (BM) in a therapeutic setting, particularly the observed lowered incidence of acute graft-versus-host disease (aGVHD) despite the infusion of human leukocyte antigen (HLA) disparate grafts. aGVHD remains a major obstacle to the broader application of allogeneic stem cell therapy and is characterized by donor $CD4^+$ T-cell activation in response to self-antigen presented by class II major histocompatibility complex (MHC) on host antigen-presenting cells (APCs). The clinical manifestation of aGVHD closely mimics the pathophysiology of autoimmune disorders with early secretion of proinflammatory cytokines including interferon γ (IFN γ), tumor necrosis factor α (TNF α), granulocyte macrophage colony-stimulating factor (GM-CSF), and interleukin (IL)-1, as well as later secretion of IL-2 by donor-derived T cells. These stimulate inflammatory cell proliferation, up-regulate MHC expression, natural killer (NK) and cytotoxic $CD8^+$ T-cell recruitment, and widespread tissue damage particularly in the skin, large intestine, and liver.

A key transcription factor in $CD4^+$ T-cell activation and the downstream target of cyclosporine A (CsA) treatment, nuclear factor of activated T cells, cytoplasmic 2 (NFATc2, also known as NFAT1) influences the expression of a wide array of cytokines, surface receptors, and cell cycle regulators associated with normal and autoimmune responses. Tandem interactions with other transcription factors, particularly the AP1 (fos/jun) complex occur at adjacent DNA binding sites located in the promoter regions of the genes encoding such factors as IFNγ, TNFα, IL-2, IL-4, IL-5, cytotoxic T-lymphocyte antigen 4 (CTLA-4), GM-CSF, and CD40L. Expression of many of these genes, specifically those associated with a Th2 or allergic response, is not severely diminished (and in some cases enhanced) in NFAT1-null mice, suggesting some level of redundancy among members of the NFAT family and their binding partners. However, NFAT1 has been shown to be required for the sustained production of IFNγ, GM-CSF, IL-3, IL-4, IL-2 (with API), and TNF-α indicating a critical role for NFAT1 in the initiation of a productive Th1 immune response.

SUMMARY

This application relates to methods of regulating immune responses and other NFAT-related processes in a lymphocyte of a subject. The methods can include modulating the activity of NFATc2 in a lymphocyte with NFATc2 mRNA antagonists (NFATc2 Translational inhibitors). In addition, methods of using NFATc2 mRNA antagonists for the treatment or prevention of an immunological incompatibility, such as graft versus host disease (GVHD) or organ transplant rejections are described herein.

In an aspect of the application, a method of decreasing NFATc2 activity in a cell, particularly a human cell, includes administering to the cell an NFATc2 mRNA antagonist at an amount effective to decrease the activity of NFATc2 in the cell. An NFATc2 antagonist can be any substance that directly or indirectly decreases NFATc2 activity. In some embodiments, an NFATc2 mRNA antagonist directly or indirectly decreases NFATc2 mRNA translation. An NFATc2 mRNA antagonist may bind to a target sequence within the NFATc2 mRNA molecule or simply obstruct other molecules that might otherwise interact with the NFATc2 mRNA. Examples of such antagonists include oligonucleotides, such as antisense oligonucleotides, and small molecules that bind to the mRNA encoding NFATc2. In certain embodiments, an NFATc2 mRNA antagonist may include a microRNA, which blocks production of NFATc2 protein through its complementary target sequence on the NFATc2 mRNA. An NFATc2 mRNA antagonist may decrease the amount of NFATc2 protein. For example, an antagonist may decrease NFATc2 translation (e.g., an antisense oligonucleotide or siRNA targeted to the NFATc2 transcript). As another example, an antagonist may increase NFATc2 mRNA degradation or otherwise decrease NFATc2 mRNA bioavailability. In certain preferred embodiments, an NFATc2 mRNA antagonist is administered to a population of T cells. For example, the cell may be present in a cell culture including hematopoietic stem cells for transplant, in an ex vivo organ, or in an organism.

In certain embodiments, an NFATc2 activity to be decreased is an activity that has a clinically or scientifically meaningful effect on a biological process. NFATc2 is known to participate in a wide range of biological processes, including immune responses, angiogenesis, skeletal muscle development and cartilage development. At the molecular level, NFATc2 activity may be assessed by detecting expression of one or more NFATc2 regulated genes (or proteins encoded therein), such as IL-2, IL-3, IL-4, IL-5, IL-13, TNF, CD40L, GM-CSF, MIP-1a, CCNA2, CCNE2 and p21. At the cellular level, NFATc2 activity may be assessed by analyzing cellular differentiation (e.g., differentiation of mesenchymal stem cell into a chondrocyte, or the activation of a T cell) or global gene or protein expression patterns.

NFATc2 mRNA antagonists may be used to modulate NFATc2 in essentially any responsive cell type. A cell may be directly or indirectly responsive to the NFATc2 mRNA antagonist. In preferred embodiments, NFATc2 mRNA antagonists are used to modulate NFATc2 in lymphocytes, such as T cells. In a particularly preferred embodiment, the cell is a transplanted cell, or a cell that is intended for use as a transplant, or a cell that is derived from a transplanted cell.

In certain aspects, the application provides a method of preventing or reducing immunological incompatibility in a subject in need thereof. A method may include administering to the subject a therapeutically effective amount of an NFATc2 mRNA antagonist. In an embodiment, the subject has or is at risk for having graft versus host disease (GVHD). A subject may be considered at risk for GVHD if the subject has received a bone marrow transplant or other transplant comprising T cells or precursors thereof (e.g., a transplant including hematopoietic stem cells). In another embodiment, the subject has or is at risk for having graft rejection.

In certain embodiments, the application provides methods for preventing or reducing immunological incompatibility in a transplant recipient by administering to the subject a therapeutically effective amount of an NFATc2 mRNA antagonist. The transplant recipient may have received a bone marrow transplant or other transplant comprising T cells or precursor cells thereof. The transplant recipient may have received a solid organ transplant. The transplant may be HLA-matched or HLA-unmatched, or allogeneic. In certain embodiments, the transplant includes hematopoietic stem cells. In certain embodiments, the transplant is a lung, heart, kidney, liver, skin, or bone marrow transplant. The transplant recipient may have received multiple organs (e.g., heart-lung transplant).

Yet another aspect of the application relates to a method of preventing graft versus host disease in a subject in need of such treatment. The method includes contacting the transplant, prior to transplantation into the subject, with an NFATc2 mRNA antagonist, thereby preventing graft versus host disease in the subject. The transplant may be HLA-matched or HLA-unmatched, or allogeneic. The transplant may include a solid organ comprising T cells or precursors thereof, such as lung, heart, kidney, liver, skin, or bone marrow. The transplant may comprise hematopoietic stem cells, such as hematopoietic stem cells from an unrelated donor, umbilical vein hematopoietic stem cells, or peripheral blood stem cells.

In certain aspects of the application, a method of treating an autoimmune disease in as subject includes administering to the subject a therapeutically effective amount of an NFATc2 mRNA antagonist.

In other aspects of the application, a method of decreasing production of an NFATc2-dependent cytokine in a subject in need of such treatment includes administering to the subject a therapeutically effective amount of an NFATc2 mRNA antagonist, thereby decreasing the production of the NFATc2-dependent cytokine.

In certain aspects, a method of preventing or reducing immune incompatibility in a subject in need thereof includes administering to the subject a therapeutically effective amount of an NFATc2 mRNA antagonist that decreases expression of NFATc2. An inhibitor RNA construct may also be referred to as a siRNA construct, including short double stranded RNAs and hairpin RNAs with a short region of internal complementarity.

The application also relates to the use of an NFATc2 mRNA antagonist for the manufacture of a medicament to treat immune incompatibilities in a subject. In one embodiment, an NFATc2 mRNA antagonist, such as an inhibitory RNA, or a small molecule, is used in the manufacture of a medicament to treat GVHD or organ transplant rejection. The invention further provides a use in manufacturing a medicament for all the methods described herein.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 3 illustrates a schematic diagram of the predicted NFATc2 3' UTR (SEQ ID NO: 2)/hsa-miR-184 (SEQ ID NO: 1) interaction.

FIG. 4 illustrates a graph showing miR-184 expression in (A) UCB CD4+ T cells; (B) UCB CD4+ T cells stimulated in vitro; and (C) AB CD4+ T cells stimulated in vitro.

FIG. 5 illustrates (A) PCR amplification of the predicted target region from UCB MNC and CD4+ cDNA; (B) a graph showing expression of luciferase in transfected UCB CD4+ cells under the influence of minimal 3' UTR (left column), the predicted miR-184 binding site from NFATc2 (middle column), or the cloned 3' UTR from NFATc2 (right column) with antisense sequence to miR-184 or irrelevant control DNA sequence (representative of 3 independent experiments); (C) a graph showing expression of luciferase in transfected AB CD4+ cells under the influence of the aforementioned 3' UTRs, exogenous pre-miR-184, and antisense to miR-184 (representative of 3 independent experiments); (D) a graph showing expression of luciferase in transfected UCB CD4+ cells under the influence of the cloned NFATc2 3' UTR (left column), the same UTR with the predicted miR-184 seed region (4 nucleotides [nt]) removed (middle column), and the same UTR with the entire predicted miR-184 binding site removed (right column) with and without antisense to miR-184 (representative of 2 independent experiments); and (E) a graph showing expression of luciferase in transfected ABCD4+ cells under the influence of the aforementioned 3' UTRs, with and without precursor to miR-184 (representative of 2 independent experiments).

FIG. 6 illustrates (A) a graph and western blot of NFAT1 protein expression in UCB CD4+ T cells 16 hours after transfection with antisense to miR-184 (n=3); (B) a graph showing NFATc2 mRNA expression in UCB CD4+ T cells; (C) a graph showing NFAT1 protein expression in AB CD4+ T cells under the following transfection with pre-miR-184 (n=4); and (D) Western blots of NFAT1 protein expression in AB CD4+ T cells 16 hours after transfection with antisense to miR-184.

FIG. 7 illustrates graphs showing (A) IL2 transcription in stimulated UCB CD4+ T cells under the influence of miR-184 antisense; and (B) IL2 transcription in stimulated AB CD4+ T cells after transfection of exogenous miR-184 precursor.

DETAILED DESCRIPTION

Figure 1:
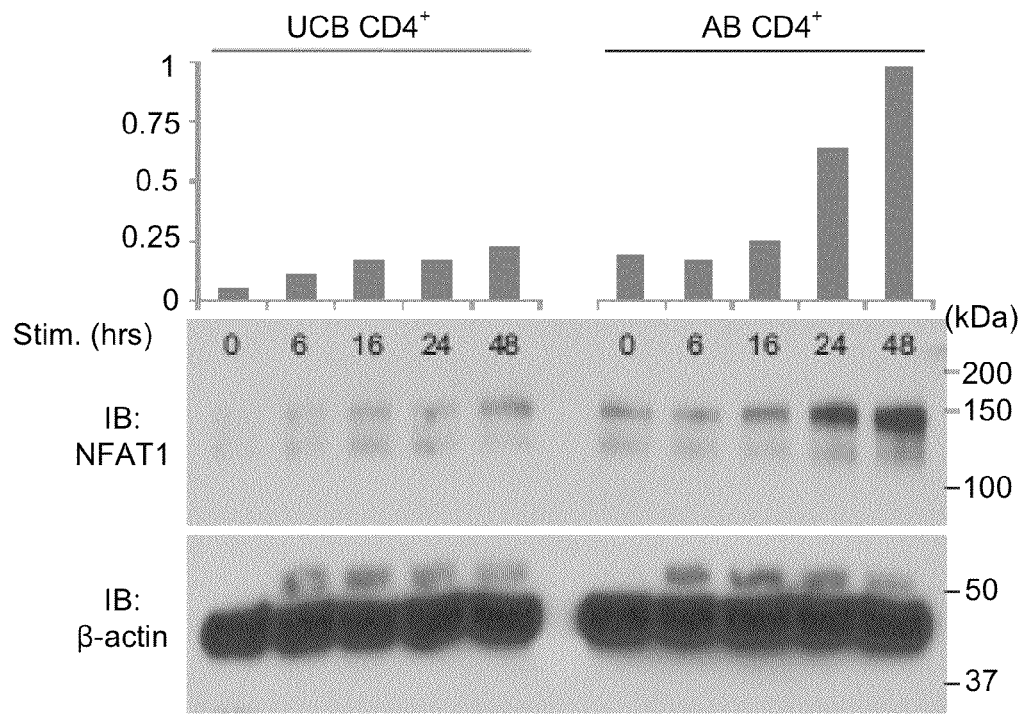
FIG. 1 illustrates a graph and western blot showing the relative NFAT1 protein and mRNA expression in stimulated UCB and AB CD4+ T cells.

This application will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, $3^{rd}$ Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. By Bonifacino, Dasso, Lippincott-Schwartz, Harford, and Yamada, John Wiley and Sons, Inc., New York, 1999.

For convenience, certain terms employed in the specification, examples, and appended claims, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited to".

The terms "polypeptide" and "protein" are used interchangeably herein.

As used herein, the term "nucleic acid" or "nucleotides" refers to polynucleotides such as deoxyribonucleic acid (DNA), and, where appropriate, ribonucleic acid (RNA). The term should also be understood to include analogs of either RNA or DNA made from nucleotide analogs, and, as applicable to the embodiment being described, single-stranded (such as sense or antisense) and double-stranded polynucleotides.

The term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, siRNAs, microRNAs, and ribonucleoproteins. The term also encompasses nucleic acids, i.e., oligonucleotides, containing known analogues of natural nucleotides, as well as nucleic acid-like structures with synthetic backbones.

The term "complementary" refers to the capacity for precise pairing between two nucleobases of a polynucleotide and its corresponding target molecule. For example, if a nucleobase at a particular position of a polynucleotide is capable of hydrogen bonding with a nucleobase at a particular position of a target polynucleotide (the target nucleic acid being a DNA or RNA molecule, for example), then the position of hydrogen bonding between the polynucleotide and the target polynucleotide is considered to be complementary. A polynucleotide and a target polynucleotide are complementary to each other when a sufficient number of complementary positions in each molecule are occupied by nucleobases, which can hydrogen bond with each other. Thus, "specifically hybridizable" and "complementary" are terms which can be used to indicate a sufficient degree of precise pairing or complementarity over a sufficient number of nucleobases such that stable and specific binding occurs between a polynucleotide and a target polynucleotide.

The terms "effective," "effective amount," and "therapeutically effective amount" refer to that amount of a NFATc2 mRNA antagonist and/or a pharmaceutical composition thereof that results in amelioration of symptoms or a prolongation of survival in a subject with a NFATc2 protein mediated disease or related disorder. A therapeutically relevant effect relieves to some extent one or more symptoms of an NFATc2 mediated disease or related disorder, or returns to normal either partially or completely one or more physiological or biochemical parameters associated with or causative of a NFATc2 mRNA mediated disease or related disorder.

The term "subject" refers to any warm-blooded organism including, but not limited to, human beings, rats, mice, dogs, goats, sheep, horses, monkeys, apes, rabbits, cattle, etc.

The term "or" is used herein to mean, and is used interchangeably with, the term "and/or," unless context clearly indicates otherwise.

The term "such as" is used herein to mean, and is used interchangeably, with the phrase "such as but not limited to".

This application relates to methods of modulating NFATc2 activity in a lymphocyte of a subject and/or administering an agent that modulates a T-cell response in a subject. In an aspect of the application, the method can include modulating NFATc2 activity in a lymphocyte by administering to the lymphocyte an NFATc2 mRNA antagonist described herein, thereby decreasing NFATc2 expression in the lymphocyte and decreasing a lymphocyte inflammatory response.

In one embodiment of these methods, the lymphocyte is a T cell. In another embodiment, decreasing NFATc2 activity comprises decreasing NFATc2 expression.

Administering an antagonist to a lymphocyte includes in some embodiments adding the antagonist to the medium in which the cell is found, such as cell culture medium when the administration is done ex vivo, such that a physical interaction is enabled. In other embodiment, such as when the antagonist is administered in vivo in a patient, the antagonist may be more generally administered to the patient. In another embodiment, the antagonist may be administered in vitro to a lymphocyte, and then introduced into the patient. The antagonist may then be further administered to the patient, such that the lymphocyte is exposed to the antagonist both in vitro and in a patient.

In one embodiment of the methods described herein to modulate the activity of NFATc2, the lymphocyte is not endogenous to the subject. In a further embodiment, the lymphocyte or a progenitor thereof may have been transplanted from another subject, or may have been cultured in vitro. For example, a lymphocyte may be generated upon differentiation of a stem cell in vitro, treated with the antagonist, and then be transplanted into the patient. The stem cell giving rise to the lymphocyte may be derived from the subject or from another subject. In some embodiments, the lymphocyte is contained in transplantable material, such a body organs or bone marrow. Body organs include lung, heart, kidney, liver, pancreas and skin.

The application further provides methods of treating or preventing immune incompatibilities. One aspect of the application provides method of preventing or reducing immune incompatibility in a subject in need thereof. The method includes administering to the subject a therapeutically effective amount of an NFATc2 mRNA antagonist.

Immune incompatibility includes cases where cells, such as human cells from another subject, are introduced into a subject which are not compatible with the subject's immune system and thus are attacked and rejected by the subject's immune system, such as in organ rejection. Immune incompatibilities also include cases where immune system cells are introduced into a subject, preferably from another subject, which are not compatible with the subject's cells and thus the introduced immune cells attack the subject's cells, such as in graft versus host disease.

Thus, in one embodiment, the subject has or is at risk for having graft versus host disease (GVHD). GVHD may be acute or it may be chronic. In another embodiment, the subject has or is at risk for graft rejection. In other embodiments, the subject is a recipient of a transplant, such as a solid organ transplant. Solid organ transplants include lung, heart, kidney, liver and skin transplants. Alternatively, the transplant may be a hematopoietic stem cell transplant, such as one from an unrelated donor. The transplant may also comprise umbilical vein hematopoietic stem cells, or peripheral blood stem cells.

The transplants described herein can be HLA matched or HLA-unmatched. In some embodiments, the transplants described herein are allogeneic transplants.

The application further provides a method of decreasing production of an NFATc2-dependent cytokine in a lymphocyte in a subject in need of such treatment, including administering to the subject a therapeutically effective amount of an NFATc2 mRNA antagonist, thereby decreasing the production of the NFATc2-dependent cytokine in the T cell. Without being bound by theory, it is believed that reducing the levels of expressed NFATc2 protein in lymphocytes (e.g., CD4+ T cells), results in lower expression of proinflammatory cytokines upon activation. In some embodiments, the NFATc2-dependent cytokine can include IFN-γ, TNF-α or IL-2.

In a further embodiment of the method for decreasing production of an NFATc2-dependent cytokine in a subject in need of such treatment, the subject is afflicted with an autoimmune disease. Autoimmune diseases include, but are not limited to primary myxoedema, thyrotoxicosis, pernicious anemia, autoimmune atrophic gastritis, Addison's disease, IDDM, Goodpasture's syndrome, myasthenia gravis, sympathetic ophthalmia, MS, autoimmune hemolytic anemia, idiopathic leucopenia, ulcerative colitis, dermatomyositis, scleroderma, mixed connective tissue disease, rheumatoid arthritis, irritable bowel syndrome, SLE, Hashimoto's disease, thyroiditis, Behcet's disease, coeliac disease/dermatitis herpetifortnis, and demyelinating disease.

In certain aspects, the invention provides a method of preventing or reducing immune incompatibility in a subject in need thereof, the method including administering to the subject a therapeutically effective amount of an NFATc2 mRNA antagonist that decreases expression of NFATc2 or an NFATc2-regulated factor. In some embodiments, the NFATc2 mRNA may include a microRNA, which blocks production of NFATc2 protein through its complementary target sequence on the NFATc2 mRNA. NFATc2 mRNA antagonist may also include a siRNA construct, having short double stranded RNAs and hairpin RNAs with a short region of internal complementarity. In a preferred embodiment, the NFATc2-regulated factor is a factor that is regulated by NFATc2 in cells of umbilical cord blood. Examples of such factors include: IL-2, IL-3, IL-4, IL-5, IL-13, GM-CSF, IFN-y, TNF-a, CD40L and MIP-1a.

The NFATc2 mRNA antagonist may be generated using the methods and procedures provided herein. For example, a miRNA can be generated which targets NFATc2 mRNA and administered in a therapeutically effective amount, through any of the methods described herein, to a subject to prevent or reduce immune incompatibility. In an embodiment, the subject is a recipient of a transplant comprising a bone marrow transplant or a solid organ transplant.

In addition to the immune system disorders described above, methods for modulating NFATc2 disclosed herein may be used to affect essentially any process in which NFATc2 participates. For example, NFATc2 participates in angiogenesis. NFATc2 signaling is necessary for the proper formation of endothelial tubes and subsequent vessel formation, particularly in postnatal mammals. Accordingly, a method for decreasing NFATc2 activity in a cell may be used to inhibit angiogenesis. In certain embodiments, modulators of NFATc2 may be used to treat or otherwise affect angiogenesis associated diseases and processes. Conditions in which it is desirable to inhibit angiogenesis (inhibit NFATc2 activity in endothelial cells by, for example, NFATc2 antagonist, include angiogenesis dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; ocular angiogenic diseases (e.g., diabetic retinopathy, retinopathy of prematurity, macular degeneration, corneal graft rejection, neovascular glaucoma) retrolental fibroplasia, rubeosis; Osler-Webber Syndrome, telangiectasia; hemophiliac joints and angiofibroma.

Additional NFATc2 regulated process may be identified by analysis of NFATc2 heterozygous and homozygous knockout mice, although the differences in NFATc2 between mice and humans are such that further research in human cells is necessary to verify and validate results obtained in mice. Additional NFATc2-regulated processes may also be identified by analysis of various human cell types in vitro or in vivo.

The NFATc2 mRNA antagonists used in the methods of described herein include any agent or substance, which decreases the activity of NFATc2 mRNA. The NFATc2 mRNA antagonist may physically bind to or hybridize with a target sequence within the NFATc2 mRNA molecule or simply obstruct other molecules that might otherwise interact with the NFATc2 mRNA, and therefore inhibit NFATc2 protein translation. The NFATc2 antagonist, for example, might bind to or hybridize with a binding site within the three prime untranslated region (3' UTR) of NFATc2 mRNA. In some embodiments the NFATc2 antagonist may bind to or hybridize with a binding site within the three prime untranslated region (3' UTR) of NFATc2 mRNA corresponding to SEQ ID NO:2.

In some embodiments, the NFATc2 antagonist can include microRNA (miRNA). The activity of specific miRNAs has been associated with a wide variety of cellular differentiation pathways, including hematopoiesis and disease states such as cancer, diabetes, and neurodegenerative diseases. These highly processed RNAs are can bind to or hybridizer with regulatory sequences in the 3' untranslated region (UTR) of target mRNAs, thus blocking gene expression by mediating mRNA degradation or translational repression.

Therefore, in some embodiments, the NFATc2 antagonist can include a miRNA that binds to or hybridizes with a binding site within the three prime untranslated region (3' UTR) of NFATc2 mRNA. For example, the NFATc2 antagonist may include a miRNA that specifically binds to or hybridizes with a binding site within the three prime untranslated region (3' UTR) of NFATc2 mRNA. In some embodiments, miRNA can bind to or hybridize with at least 15 consecutive nucleotides of SEQ ID NO:2. In other embodiments, the miRNA is a synthetic precursor miRNA. In still other embodiments, the miRNA can consist essentially of about 10 to about 30 nucleotides in length (e.g., about 15 to about 25 nucleotides in length) and specifically bind to or hybridize with at least about 15 consecutive nucleotides of nucleotide sequence that is substantially homologous to SEQ ID NO: 2 to decrease NFATc2 activity when administered to a lymphocyte.

By substantially homologous to SEQ ID NO: 2, it is meant the nucleotide sequence has at least about 80%, about 90%, about 95%, about 96%, about 97%, about 98%, about 99% or about 100% sequence identity with at least 15 consecutive nucleotides of the nucleotide sequence of SEQ ID NO: 2.

In other embodiments, the NFATc2 antagonist can include a microRNA having a nucleotide sequence that is substantially homologous to SEQ ID NO:1. By substantially homologous to SEQ ID NO: 1, it is meant the nucleotide sequence has at least about 80%, about 90%, about 95%, about 96%, about 97%, about 98%, about 99% or about 100% sequence identity with the nucleotide sequence of SEQ ID NO: 1 and binds to or hybridizes with SEQ ID NO: 2 to decrease, inhibit, or prevent NAFTc2 protein translation. For example, miR-184 microRNA can bind to a binding site within the three prime untranslated region (3' UTR) of NFATc2 mRNA corresponding to SEQ ID NO:2, thereby inhibiting NFATc2 protein translation. In addition, miRNA species for use in the present invention may bind to binding sites proximal to and overlapping with the three prime untranslated region (3' UTR) of NFATc2 mRNA corresponding to SEQ ID NO:2. Additional miRNA species for use in the present invention can be readily identified in silico by determining miRNA sequences predicted to bind to the 3' UTR of NFATc2 mRNA.

In some embodiments, NFATc2 mRNA antagonists include RNA interference (RNAi) reagents to induce knockdown of NFATc2 mRNA. RNAi is a process of sequence-specific post-transcriptional gene repression, which can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of, in some instances, as few as 21 to 22 base pairs in length. Furthermore, RNAi may be effected by introduction or expression of relatively short homologous dsRNAs. Indeed the use of relatively short homologous dsRNAs may have certain advantages as discussed below.

Mammalian cells have at least two pathways that are affected by double-stranded RNA (dsRNA). In the RNAi (sequence-specific) pathway, the initiating dsRNA is first broken into short interfering (si)RNAs, as described above. The siRNAs have sense and antisense strands of about 21 nucleotides that form approximately 19 nucleotide siRNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length. The nonspecific effects occur because dsRNA activates two enzymes: PKR, which in its active form phosphorylates the translation initiation factor eIF2 to shut down all protein synthesis, and 2',5' oligoadenylate synthetase (2',5'-AS), which synthesizes a molecule that activates Rnase L, a nonspecific enzyme that targets all mRNAs. The nonspecific pathway may represent a host response to stress or viral infection, and, in general, the effects of the nonspecific pathway are preferably minimized under preferred methods of the present invention. Significantly, longer dsRNAs appear to be required to induce the nonspecific pathway and, accordingly, dsRNAs shorter than about 30 bases pairs are preferred to effect gene repression by RNAi, (see Hunter et al. (1975) J Biol Chem 250: 409-17; Manche et al. (1992) Mol Cell Biol 12: 5239-48; Minks et al. (1979) J Biol Chem 254: 10180-3; and Elbashir et al. (2001) Nature 411: 494-8).

RNAi has been shown to be effective in reducing or eliminating the expression of a gene in a number of different organisms including Caenorhabditis elegans (see e.g., Fire et al. (1998) Nature 391: 806-11), mouse eggs and embryos (Wianny et al. (2000) Nature Cell Biol 2: 70-5; Svoboda et al. (2000) Development 127: 4147-56), and cultured RAT-1 fibroblasts (Bahramina et al. (1999) Mol Cell Biol 19:274-83), and appears to be an anciently evolved pathway available in eukaryotic plants and animals (Sharp (2001) Genes Dev. 15: 485-90). RNAi has proven to be an effective means of decreasing gene expression in a variety of cell types including HeLa cells, NIH/3T3 cells, COS cells, 293 cells and BHK 21 cells, and typically decreases expression of a gene to lower levels than that achieved using antisense techniques and, indeed, frequently eliminates expression entirely (see Bass (2001) Nature 411: 428-9). In mammalian cells, siRNAs are effective at concentrations that are several orders of magnitude below the concentrations typically used in antisense experiments (Elbashir et al. (2001) Nature 411: 494-8).

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides of the invention may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al. (2001) Nature 411: 494-8). Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable to the skilled artisan. Exemplary dsRNAs may be synthesized chemically or produced in vitro or in vivo using appropriate expression vectors. Exemplary synthetic RNAs include 21 nucleotide RNAs chemically synthesized using methods known in the art (e.g., Expedite RNA phophoramidites and thymidine phosphoramidite (Proligo, Germany). Synthetic oligonucleotides are preferably deprotected and gel-purified using methods known in the art (see e.g., Elbashir et al. (2001) Genes Dev. 15: 188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence.

In certain embodiments, any of the above RNA species for use as an NFATc2 mRNA antagonist can be designed to include a portion of a nucleic acid sequence that hybridizes, under stringent and/or physiological conditions to the NFATc2 mRNA sequence, such as Genbank Accession No: NM_012340 and NM_173091.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference. Messenger RNA (mRNA) is generally thought of as a linear molecule, which contains the information for directing protein synthesis within the sequence of ribonucleotides, however studies have revealed a number of secondary and tertiary structures that exist in most mRNAs. Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al. (1989) Proc. Natl. Acad. Sci. USA 86:7706 (1989); and Turner et al. (1988) Annu. Rev. Biophys. Biophys. Chem. 17:167). The rules are useful in identification of RNA structural elements and, in particular, for identifying single stranded RNA regions which may represent preferred segments of the mRNA to target for silencing RNAi, ribozyme or antisense technologies. Accordingly, preferred segments of the mRNA target can be identified for design of the RNAi mediating dsRNA oligonucleotides as well as for design of appropriate ribozyme and hammerheadribozyme compositions of the invention.

The dsRNA oligonucleotides may be introduced into the cell by transfection with a heterologous target gene using carrier compositions such as liposomes, which are known in the art—e.g., Lipofectamine 2000 (Life Technologies) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP-encoding pAD3 (Kehlenback et al. (1998) J Cell Biol 141: 863-74). Further compositions, methods and applications of RNAi technology are provided in U.S. Pat. Nos. 6,278,039, 5,723,750 and 5,244,805, which are incorporated herein by reference.

Ribozyme molecules designed to catalytically cleave IFN-y encoding mRNAs, or mRNAs encoding other members of the IFN-y signaling pathway (see, e.g., PCT International Publication WO90/11364, published Oct. 4, 1990; Sarver et al. (1990) Science 247:1222-1225 and U.S. Pat. No. 5,093,246). Ribozymes are enzymatic RNA molecules capable of catalyzing the specific cleavage of RNA. (For a review, see Rossi (1994) Current Biology 4: 469-471). The mechanism of ribozyme action involves sequence specific hybridization of the ribozyme molecule to complementary target RNA, followed by an endonucleolytic cleavage event.

While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art and is described more fully in Haseloff and Gerlach (1988) Nature 334:585-591; and see PCT Appln. No. WO89/05852, the contents of which are incorporated herein by reference). Hammerhead ribozyme sequences can be embedded in a stable RNA such as a transfer RNA (tRNA) to increase cleavage efficiency in vivo (Perriman et al. (1995) Proc. Natl. Acad. Sci. USA, 92: 6175-79; de Feyter, and Gaudron, Methods in Molecular Biology, Vol. 74, Chapter 43, "Expressing Ribozymes in Plants", Edited by Turner, P. C, Humana Press Inc., Totowa, N.J.). In particular, RNA polymerase III-mediated expression of tRNA fusion ribozymes are well known in the art (see Kawasaki et al. (1998) Nature 393: 284-9; Kuwabara et al. (1998) Nature Biotechnol. 16: 961-5; and Kuwabara et al. (1998) Mol. Cell 2: 617-27; Koseki et al. (1999) J Virol 73: 1868-77; Kuwabara et al. (1999) Proc Natl Acad Sci USA 96: 1886-91; Tanabe et al. (2000) Nature 406: 473-4). There are typically a number of potential hammerhead ribozyme cleavage sites within a given target cDNA sequence. Preferably the ribozyme is engineered so that the cleavage recognition site is located near the 5' end of the target mRNA—to increase efficiency and minimize the intracellular accumulation of non-functional mRNA transcripts. Furthermore, the use of any cleavage recognition site located in the target sequence encoding different portions of the C-terminal amino acid domains of, for example, long and short forms of target would allow the selective targeting of one or the other form of the target, and thus, have a selective effect on one form of the target gene product.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA. The present invention extends to ribozymes which hybridize to a sense mRNA encoding NFATc2 protein when an NFATc2 mRNA antagonist is desired.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324: 429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene or nucleic acid sequence.

Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target messages and inhibit translation. Because ribozymes, unlike antisense molecules, are catalytic, a lower intracellular concentration is required for efficiency.

In certain embodiments, a ribozyme may be designed by first identifying a sequence portion sufficient to cause effective knockdown by RNAi. The same sequence portion may then be incorporated into a ribozyme.

In a long target RNA chain, significant numbers of target sites are not accessible to the ribozyme because they are hidden within secondary or tertiary structures (Birikh et al. (1997) Eur J Biochem 245: 1-16). To overcome the problem of target RNA accessibility, computer generated predictions of secondary structure are typically used to identify targets that are most likely to be single-stranded or have an "open" configuration (see Jaeger et al. (1989) Methods Enzymol 183: 281-306). Other approaches utilize a systematic approach to predicting secondary structure which involves assessing a huge number of candidate hybridizing oligonucleotides molecules (see Milner et al. (1997) Nat Biotechnol 15: 537-41; and Patzel and Sczakiel (1998) Nat Biotechnol 16: 64-8). Additionally, U.S. Pat. No. 6,251,588, the contents of which are hereby incorporated herein, describes methods for evaluating oligonucleotide probe sequences so as to predict the potential for hybridization to a target nucleic acid sequence. The method of the invention provides for the use of such methods to select preferred segments of a target mRNA sequence that are predicted to be single-stranded and, further, for the opportunistic utilization of the same or substantially identical target mRNA sequence, preferably comprising about 10-20 consecutive nucleotides of the target mRNA, in the design of both the RNAi oligonucleotides and ribozymes of the invention.

In certain embodiments, expression of the "target gene", for example, NFATc2, may be inhibited by an inhibitor RNA that is a single-stranded RNA molecule containing an inverted repeat region that causes the RNA to self-hybridize, forming a hairpin structure (a so-called "hairpin RNA" or "shRNA"). shRNA molecules of this type may be encoded in RNA or DNA vectors. The term "encoded" is used to indicate that the vector, when acted upon by an appropriate enzyme, such as an RNA polymerase, will give rise to the desired shRNA molecules (although additional processing enzymes may also be involved in producing the encoded shRNA molecules). The expression of shRNAs may be constitutive or regulated in a desired manner.

A double-stranded structure of a shRNA is formed by a single self-complementary RNA strand. RNA duplex formation may be initiated either inside or outside the cell. Inhibition is sequence-specific in that nucleotide sequences corresponding to the duplex region of the RNA are targeted for genetic inhibition. shRNA constructs containing a nucleotide sequence identical to a portion, of either coding or non-coding sequence, of the target gene are preferred for inhibition. RNA sequences with insertions, deletions, and single point mutations relative to the target sequence have also been found to be effective for inhibition. Because 100% sequence identity between the RNA and the target gene is not required to practice the present invention, the invention has the advantage of being able to tolerate sequence variations that might be expected due to genetic mutation, strain polymorphism, or evolutionary divergence. Sequence identity may be optimized by sequence comparison and alignment algorithms known in the art, (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). In certain preferred embodiments, the length of the duplex-forming portion of a shRNA is at least 20, 21 or 22 nucleotides in length, e.g., corresponding in size to RNA products produced by Dicer dependent cleavage. In certain embodiments, the shRNA construct is at least 25, 50, 100, 200, 300 or 400 bases in length. In certain embodiments, the shRNA construct is 400-800 bases in length. shRNA constructs are highly tolerant of variation in loop sequence and loop size. An endogenous RNA polymerase of the cell may mediate transcription of a shRNA encoded in a nucleic acid construct. The shRNA construct may also be synthesized by a bacteriophage RNA polymerase (e.g., T3, T7, SP6) that is expressed in the cell.

In another embodiment, the NFATc2 mRNA antagonist comprises a small molecule or drug. In a specific embodiment, the small molecule or drug binds to a binding site within the three prime untranslated region (3' UTR) of NFATc2 mRNA corresponding to SEQ ID NO:2. In another embodiment, the small molecule or drug simply obstructs or blocks interaction with other molecules that might otherwise interact with NFATc2 mRNA in the facilitation of NFATc2 protein translation. Such small molecules may be identified using common screening methods known to one skilled in the art.

Various methods of transferring or delivering DNA to cells for expression of the gene product protein which can be easily adapted for the expression of an NFATc2 mRNA antagonist are disclosed in Gene Transfer into Mammalian Somatic Cells in vivo, N. Yang, Crit. Rev. Biotechn. 12(4):335-356 (1992), which is hereby incorporated by reference.

Gene transfer methods for gene therapy fall into three broad categories-physical (e.g., electroporation, direct gene transfer and particle bombardment), chemical (lipid-based carriers, or other non-viral vectors) and biological (virus-derived vector and receptor uptake). For example, non-viral vectors may be used which include liposomes coated with DNA. Such liposomal DNA complexes may be directly injected intravenously into the patient. It is believed that the liposomal DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then re-implanted in the patient. In in vitro gene transfer, the transformed cells are cells growing in culture, such as tissue culture cells, and not cells particularly derived from a given patient. These "laboratory cells" are transfected, the transfected cells are selected and expanded for either implantation into a patient or for other uses. These cells can then secrete the NFATc2 mRNA antagonist in the patient. Depending on the half-life of the cells and the desired length of therapeutic treatment, this process of implanting transfected cells into the patient may be repeated as desired.

In one embodiment, the cells transfected with the DNA which encodes the NFATc2 mRNA antagonist are cells which are intended to be transplanted into a patient, such as cells from a bone marrow transplant or cells from a solid organ transplant. For example, cells from a bone marrow transplant can be transfected with an NFATc2 mRNA antagonist in vitro prior to grafting into a patient, or a solid organ can be transfused with the DNA encoding the NFATc2 mRNA antagonist in an appropriate transfecting composition prior to transplanting into the patient.

In vivo gene transfer involves introducing the DNA into the cells of the patient when the cells are already within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of NFATc2 mRNA antagonist DNA.

Chemical methods of gene therapy may involve a lipid based compound, not necessarily a liposome, to ferry the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane.

The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Another method, ligand mediated gene therapy, involves complexing the DNA with specific ligands to form ligand-DNA conjugates, to direct the DNA to a specific cell or tissue. Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs.

Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs. In some embodiments of the invention, lymphocytes can be transfected with synthetic precursor miRNA via electroporation. For example, T cells can be transfected with synthetic precursor mir-184 via AMAXA NUCLEOFECTOR (AMAXA, Gaithersburg, Md.).

Carrier mediated gene transfer in vivo can be used to transfect foreign DNA into cells. The carrier-DNA complex can be conveniently introduced into body fluids or the bloodstream and then site specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoprotein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

The NFATc2 mRNA antagonist can be administered to lymphocytes, such as T cells, either in vivo or in vitro. The cell can be derived from a human subject, from a known cell line, or from some other suitable source. One example of a cell can include a T cell located in, for example, a human subject. The cell may be isolated or, alternatively, associated with any number of identical, similar, or different cell types. Where the cell comprises a lymphocyte, for example, the lymphocyte may be associated with a costimulatory cell, such as an APC. The T cell can also comprise a T cell in the subject and the NFATc2 mRNA antagonist can be used to treat a T cell mediated disease in the subject. The at least one the NFATc2 mRNA antagonist can be administered to the subject to treat the T cell mediated disease in the subject using any one or combination of known techniques.

In one aspect of the invention, the NFATc2 mRNA antagonist can be administered directly or locally to a site of T cell mediated disease in the subject. Local or direct administration of the NFATc2 mRNA antagonist into and/or about the periphery of the disease site is advantageous because the NFATc2 mRNA antagonist localizes at the disease site being treated and does not substantially affect the subject's innate complement system.

In another aspect of the invention, the NFATc2 mRNA antagonist can be administered to the subject systemically by, for example, intravenous, intraarterial, intraperitoneal, intramuscular, subcutaneous, intrapleural, intrathecal, oral or nasal route, to treat the T cell mediated disease or related disorder in the subject. When administered systemically, the NFATc2 mRNA antagonist is preferably targeted to a disease site to ensure that the NFATc2 mRNA antagonist does not adversely affect other normal cells expressing NFATc2, and to potentially mitigate adverse systemic effects on the subject's complement system. Several systems have been developed in order to restrict the delivery of the NFATc2 mRNA antagonist to the disease site. With the identification of cells specific receptors and antigens on mammalian cells, it is possible to actively target the NFATc2 mRNA antagonist using ligand or antibody bearing delivery systems. Alternatively, the NFATc2 mRNA antagonist can be loaded on a high capacity drug carriers, such as liposomes or conjugated to polymer carriers that are either directly conjugated to targeting proteins/peptides or derivatised with adapters conjugated to a targeting moiety.

Examples of antibodies which can be potentially conjugated the NFATc2 mRNA antagonist to target the NFATc2 mRNA antagonist to the T cell mediated disease site include, but are not limited to, anti-CD20 antibodies (e.g., Rituxan, Bexxar, Zevalin), anti-Her2/neu antibodies (e.g., Herceptin), anti-CD33 antibodies (e.g., Mylotarg), anti-CD52 antibodies (e.g., Campath), anti-CD22 antibodies, anti-CD25 antibodies, anti-CTLA-4 antibodies, anti-EGF-R antibodies (e.g.

Erbitux), anti-VEGF antibodies (e.g. Avastin, VEGF Trap) anti-HLA-DR10β antibodies, anti-MUC1 antibodies, anti-CD40 antibodies (e.g. CP-870,893), anti-Treg cell antibodies (e.g., MDX-010, CP-675,206), anti-GITR antibodies, anti-CCL22 antibodies, and the like.

The NFATc2 mRNA antagonist, whether administered locally and/or systemically, can also be provided in a pharmaceutically acceptable composition. The phrase "pharmaceutically acceptable" should be understood to mean a material which is not biologically or otherwise undesirable, i.e., the material may be incorporated into an antiviral composition and administered to a subject without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. Sterile phosphate-buffered saline is one example of a pharmaceutically acceptable carrier. Other suitable carriers are well-known to those in the art. See, for example, REMINGTON'S PHARMACEUTICAL SCIENCES, 19th Ed. (1995), and later editions.

In general, the dosage of the NFATc2 mRNA antagonist will vary depending upon such factors as the subject's age, weight, height, sex, general medical condition and previous medical history. Typically, it is desirable to provide the subject with a dosage of the NFATc2 mRNA antagonist which is in the range of from about 1 pg/kg to 10 mg/kg (amount of agent/body weight of patient), although a lower or higher dosage also may be administered as circumstances dictate. The specific dosage or amount of the NFATc2 mRNA antagonist administered to a lymphocyte (e.g., T cell) will be that amount effective to reduce or inhibit NFATc2 activity in the lymphocyte.

In accordance with the invention, T-cells for use in the present invention can be isolated using various methods. In humans, T-cells may be isolated from a peripheral blood sample taken from a subject. Once the T cells are isolated, they can then be cultured, for example in a suitable growth medium, and administered the NFATc2 mRNA antagonist to inhibit NFATc2 activity in the cells. "Cultured" and "maintained in culture" are interchangeably used when referring to the in vitro cultivation of cells and include the meaning of expansion or maintenance of a cell population under conditions known to be optimal for cell growth. The cell culture is maintained under culture conditions including suitable temperature, pH, nutrients, and proper growth factors which favor the in vitro expansion and survival of T-cells.

The T-cells administered the NFATc2 mRNA antagonist of the present invention can be used to prevent local and systemic organ and tissue destruction in cell therapies aimed at alleviating T cell mediated diseases. According to the method, activated T-cells described above having been expanded ex vivo, are reinfused into the host subject for the treatment of T-cell related diseases and disorders.

The method of treating a T cell mediated disease in a subject includes administering a therapeutically effective amount of the NFATc2 mRNA antagonist treated T-cells to the subject. The activated T-cells of the present invention may originate from a subject into which they are implanted (reimplantation) or from elsewhere (transplantation). In some aspects, a subject is administered T-cells derived from the subject's own body because the risk of transmission of an infection such as HIV is eliminated and the risk of triggering an immune system-mediated rejection reaction is reduced.

In general, the T-cells treated with the NFATc2 mRNA antagonist are administered (e.g., implanted) into the mammalian subject by methods well known in the art. The T-cells treated with the NFATc2 mRNA antagonist of the present invention may be introduced into the subject by any suitable route whether that route is enteral or parenteral, for example, intravenous or intramuscular. In one exemplary embodiment, the T-cells are administered directly to an area of a T cell mediated disease.

The term "T cell mediated disease" refers to diseases and disorders in which an aberrant immune reaction involves T cell-mediated immune mechanisms, as opposed to humoral immune mechanisms. Thus, the methods of the invention pertain to treatments of immune disorders in which tissue destruction is primarily mediated through activated T cells and immune cells other than B-lymphocytes.

For example, the methods of the present invention can be used in the treatment of autoimmune conditions or diseases such as inflammatory diseases (for example rheumatoid arthritis, uveitis, inflammatory bowel disease, asthma, glomerulonephritis, lung fibrosis, Wegener's granulomatosis; chronic obstructive pulmonary disease (COPD); acute respiratory distress syndrome (ARDS); transfusion-related acute lung injury (TRALI); ischemia/reperfusion acute lung injury; and Goodpasture's disease), granulocytopenia, multiple sclerosis, myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD) and Alzheimer's disease (AD), psoriasis, hypersensitivity reactions of the skin, sepsis, atherosclerosis, ischemia-reperfusion injury, myocardial infarction, restenosis, vasculitis, systemic lupus erythematosus (SLE), and insulin-dependent diabetes. The methods of the present invention can also be used for the prevention or treatment of the acute rejection of transplanted organs where administration of a therapeutic described herein, may occur during the acute period following transplantation or as long-term post transplantation therapy.

T cell mediated diseases contemplated by the present invention include T cell mediated autoimmune diseases or disorders. The language "autoimmune disorder" is intended to include disorders in which the immune system of a subject reacts to autoantigens, such that significant tissue or cell destruction occurs in the subject. The term "autoantigen" is intended to include any antigen of a subject that is recognized by the immune system of the subject. The terms "autoantigen" and "self-antigen" are used interchangeably herein. The term "self" as used herein is intended to mean any component of a subject and includes molecules, cells, and organs. Autoantigens may be peptides, nucleic acids, or other biological substances.

Even though the methods of the invention are intended for treatment of immune disorders mediated by cells other than B cells, the immune disorders may include autoimmune diseases and disorders characterized by the presence of autoantibodies. For example, multiple sclerosis, a T cell mediated autoimmune disorder, which can be treated by a method of the invention, is frequently associated with the presence of autoantibodies to components of the central nervous system, such as myelin basic protein. Non limiting examples of T cell mediated autoimmune disorders that can be treated by the methods of the invention include multiple sclerosis, EAE, diabetes type I, oophoritis, and thyroiditis.

The present invention additionally provides methods of preventing or reducing immune incompatibility in a subject in need thereof, the method comprising administering to the subject a therapeutically effective amount of an antagonist. In one embodiment, the subject has or is at risk for having graft versus host disease (GVHD). The methods described herein to treat or prevent GVHD may be applied to acute and to chronic GVHD. Acute GVHD typically occurs within the first three months following a transplant. Chronic GVHD occurs two or three months after a transplant and may include symptoms similar to autoimmune diseases and rashes, and may include liver, stomach and intestinal problems.

The methods of the invention are suitable for the prevention and treatment of GVHD in the course of bone marrow transplantation in patients suffering from diseases curable by bone marrow transplantation, including leukemias, such as acute lymphoblastic leukemia (ALL), acute nonlymphoblastic leukemia (ANLL), acute myelocytic leukemia (AML) and chronic myelocytic leukemia (CML), severe combined immunodeficiency syndromes (SCID), osteopetrosis, aplastic anemia, Gaucher's disease, thalassemia and other congenital or genetically-determined hematopoietic or metabolic abnormalities. The need for a bone marrow stem cell transplant arises because the only treatment that appears to have a chance of killing the disease in the host also kills the host's cellular immune system. Thus, the patient or host is treated to kill the target disease, and as a result of such treatment, the host's cellular immune system is also killed. Common methods of treatment include radiation treatment and chemotherapy, either alone or together, with or without accompanying surgery After such treatment, it is necessary to provide the patient with a means for regenerating the patient's immune system. The bone marrow or bone marrow hematopoietic stem cell transplant provides the basis for this immune system regeneration. The donor is treated to enrich his or her blood with bone marrow stem cells. The donor's blood is drawn and is centrifuged to separate the white blood cells, which include the desired stem cells necessary to regenerate the host's immune system from the rest of the blood. The separated white blood cells will also include the donor's T-cells. The separated white blood cells from the transplant innoculum are then infused into the host. After infusion into the host, the infused or transplanted stem cells will seed the host's bone marrow and will differentiate into different blood cell types. This regeneration of the immune system, i.e., the production by the host of T-cells which can attack aberrant cells, such as infected cells, takes several weeks to several months In one embodiment, a therapeutically effective of an NFATc2 mRNA antagonist is administered to the subject under a suitable conditioning regimen, such as from day-2 prior to the transplantation day, and then for another 60-100, at least 60, days, after the transplantation day. As used herein, the term therapeutically effective amount means an amount of NFATc2 mRNA antagonist of the pharmaceutical composition or method that is sufficient to show a meaningful patient benefit, i.e., a reduction in the incidence or severity of acute or chronic graft-versus-host disease compared to that expected for a comparable group of patients not receiving the NFATc2 mRNA antagonist, as determined by the attending physician. When applied to an individual active ingredient administered alone, the term refers to that ingredient alone. When applied to a combination, the term refers to combined amounts of the active ingredients that result in the therapeutic effect, whether administered in combination, serially, or simultaneously. Ultimately, the attending physician will decide on the appropriate duration of and dosage of the NFATc2 mRNA antagonist treatment.

The methods described herein for treating or preventing GVHD are in some embodiments used in combination with other treatments. In one embodiment, a patient suffering or at risk of developing chronic GVHD can be treated with steroids such as cyclosporine, prednisone, and ozothioprine, or with cyclosporine and methotrexate, while at the same time be treated using one NFATc2 mRNA antagonists.

In one embodiment, the NFATc2 mRNA antagonist administered to a patient to prevent or treat GVHD is administered in a dosage where the GVHD is reduced but where it is not completely eliminated. A low level of GVHD is in some cases beneficial for the stem cell graft to colonize the patient bone marrow. Additional, the presence of active T-cells from a donor may help eliminate tumorigenic cells in a subject, such as a subject afflicted with leukemia. The invention also provides a method of preventing graft versus host disease in a subject in need of such treatment, the method comprising contacting a transplant, prior to transplantation into the subject, with an NFATc2 mRNA antagonist, thereby preventing graft versus host disease in the subject. In one embodiment, a therapeutically effective amount of an NFATc2 mRNA antagonist is administered to the transplant innoculum prior to transplantation into the subject. In another embodiment, the transplant innoculum is depleted of T cells, such as by centrifugation, and the graft is then treated with IFN-y antagonists prior to implantation into the patient or host.

The invention also provides methods of preventing or reducing immune incompatibility in a subject in need thereof, the method including administering to the subject a therapeutically effective amount of an NFATc2 mRNA antagonist, wherein the subject is a recipient of a solid organ transplant. In one embodiment, the organ transplant comprises a lung, heart, kidney, liver, or skin. The transplant may be HLA matched or it may be unmatched.

In one embodiment, the solid organ is treated with an NFATc2 mRNA antagonist, such as by perfusion, prior to transplantation. In another embodiment, the NFATc2 mRNA antagonist is administered to the subject as described for treating or preventing GVHD, but wherein a therapeutically effective amount used refers to the amount of NFATc2 mRNA antagonist sufficient to show a meaningful patient benefit, i.e., a reduction in the incidence or severity of organ rejection compared to that expected for a comparable group of patients not receiving the NFATc2 mRNA antagonist, as determined by the attending physician.

Another aspect of the invention provides methods of preventing or reducing immune incompatibility in a subject in need thereof, the method including administering to the subject a therapeutically effective amount of an NFATc2 mRNA antagonist that decreases expression of NFATc2 and/or a NFATc2-regulated factor. The NFATc2 mRNA antagonist can be any of the variants described in the present invention. In one embodiment, the inhibitor is a miRNA. The NFATc2 mRNA antagonist may be administered to the subject locally, such as at the site of an organ transplant, or alternatively it may be administered systemically, or both.

In one embodiment, the subject has or is at risk for having graft versus host disease, such as a recipient of a hematopoietic stem cell transplant. Hematopoietic stem cell transplant as used herein may comprises hematopoietic stem cells from an unrelated donor, umbilical vein hematopoietic stem cells, or peripheral blood stem cells.

In another embodiment, the subject has or is at risk for having graft rejection, such as a subject who is the recipient of a solid organ transplant. Transplants may be is HLA-matched or HLA-unmatched, and they may be allogeneic.

The invention also provides methods of treating an autoimmune disease in a subject in need thereof, the method comprising administering to the subject a therapeutically effective amount of an NFATc2 mRNA antagonist. In one embodiment, the autoimmune disease is selected from among the following: primary myxoedema, thyrotoxicosis, pernicious anemia, autoimmune atrophic gastris, Addison's disease, IDDM, Goodpasture's syndrome, myasthenia gravis, sympathetic ophthalmia, MS, autoimmune haemolytic anaemia, idiopathic leucopenia, ulcerative colitis, derinatomyositis, sclerodenna, mixed connective tissue disease, rheumatoid arthritis, irritable bowel syndrome, SLE, Hashimoto's disease, thyroiditis, Behcet's disease, coeliac disease/dermatitis herpetifortnis, and demyelinating disease.

The methods described herein comprise the administration of NFATc2 mRNA antagonists. In preferred embodiments, the antagonists described herein are formulated into pharmaceutical compositions. For example, the antagonists and their physiologically acceptable salts and solvates may be formulated for administration by, for example, by aerosol, intravenous, oral or topical route. The administration may comprise intralesional, intraperitoneal, subcutaneous, intramuscular or intravenous injection; infusion; liposome-mediated delivery; topical, intrathecal, gingival pocket, per rectum, intrabronchial, nasal, transmucosal, intestinal, oral, ocular or otic delivery.

As for the amount of the compound and/or antagonist for administration to the subject, one skilled in the art may readily determine the appropriate amount. As used herein, a dose or amount would be one in sufficient quantities to either inhibit the disorder, treat the disorder, treat the subject or prevent the subject from becoming afflicted with the disorder. This amount may be considered an effective amount. A person of ordinary skill in the art can perform simple titration experiments to determine what amount is required to treat the subject. The dose of the composition of the invention will vary depending on the subject and upon the particular route of administration used. In one embodiment, the dosage can range from about 0.1 to about 100,000 µg/kg body weight of the subject. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

The effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective. The effective amount will be known to one of skill in the art; it will also be dependent upon the form of the compound, the size of the compound and the bioactivity of the compound. One of skill in the art could routinely perform empirical activity tests for a compound to determine the bioactivity in bioassays and thus determine the effective amount. In one embodiment of the above methods, the effective amount of the compound comprises from about 1.0 ng/kg to about 100 mg/kg body weight of the subject. In another embodiment of the above methods, the effective amount of the compound includes from about 100 ng/kg to about 50 mg/kg body weight of the subject. In another embodiment of the above methods, the effective amount of the compound comprises from about 1 µg/kg to about 10 mg/kg body weight of the subject. In another embodiment of the above methods, the effective amount of the compound comprises from about 100 µg/kg to about 1 mg/kg body weight of the subject.

As for when the compound, compositions and/or antagonist is to be administered, one skilled in the art can determine when to administer such compound and/or antagonist. The administration may be constant for a certain period of time or periodic and at specific intervals. The compound may be delivered hourly, daily, weekly, monthly, yearly (e.g., in a time release form) or as a one time delivery. The delivery may be continuous delivery for a period of time, e.g., intravenous delivery. In one embodiment of the methods described herein, the agent is administered at least once per day. In one embodiment of the methods described herein, the antagonist is administered daily. In one embodiment of the methods described herein, the antagonist is administered every other day. In one embodiment of the methods described herein, the antagonist is administered every 6 to 8 days. In one embodiment of the methods described herein, the antagonist is administered weekly.

The following examples are for the purpose of illustration only and are not intended to limit the scope of the claims, which are appended hereto.

EXAMPLE

This example shows that a specific microRNA, miR-184, inhibits NFAT1 protein expression elicited by UCB CD4$^+$ T cells. Endogenous expression of miR-184 in UCB is 58.4-fold higher compared with AB CD4$^+$ T cells, and miR-184 blocks production of NFAT1 protein through its complementary target sequence on the NFATc2 mRNA without transcript degradation. Furthermore, its negative effects on NFAT1 protein and downstream interleukin-2 (IL-2) transcription are reversed through antisense blocking in UCB and can be replicated via exogenous transfection of precursor miR-184 into AB CD4$^+$ T cells.

Methods

Cell Isolation and Culture

Whole blood was obtained from umbilical cords immediately after delivery or by venipuncture from healthy adult donors, and informed consent was obtained in accordance with the Declaration of Helsinki. Mononuclear cells were isolated after centrifugation through Ficoll-Paque PLUS (GE Healthcare, Piscataway, N.J.) per the manufacturer's instructions. CD4$^+$ T cells were then isolated via magnetic bead-labeling and separation (AutoMACS; Miltenyi Biotec, Auburn, Calif.) by first depleting the sample of CD14$^+$ monocytes and then positively selecting for CD4$^+$ cells, per the manufacturer's recommendations. CD45RA$^+$ naive T cells were isolated via the Naive Human T-cell Isolation kit (Miltenyi Biotec). Purity as measured by flow cytometry was greater than 90%. CD4$^+$ T cells were cultured in RPMI 1640 medium containing 10% fetal bovine serum (Gibco, Carlsbad, Calif.) supplemented with 2 mM L-glutamine (Gibco). Where applicable, T cells were stimulated in wells containing 1 µg/mL plate-bound αCD3 antibody and 5 µg/mL soluble αCD28 antibody (BD Biosciences, San Jose, Calif.).

Western Blot Analysis

Cells were pelleted and lysed with radioimmunoprecipitation assay (RIPA) buffer. After centrifugation, lysate supernatants were assayed for total protein content by modified Bradford assay (Bio-Rad Laboratories, Hercules, Calif.) per the manufacturer's instructions. The lysates were standardized for protein concentration, diluted with 4× sodium dodecyl sulfate (SDS) loading buffer containing β-mercaptoethanol and heated to 95° C. for 5 minutes. Equal volumes of samples were loaded into the wells of a 7.5% polyacrylamide SDS gel and run per standard protocol. The gel was then transferred to an Immobilon-P polyvinylidene fluoride (PVDF) membrane (Millipore, Billerica, Mass.) via standard wet-transfer protocol. Membrane was blocked with 5% dry milk, cut, and probed with primary antibodies to NFAT1 (no.

610703; BD Transduction Laboratories, San Jose, Calif.), β-actin (no. A5441; Sigma-Aldrich, St Louis, Mo.), and horseradish peroxidase (HRP)-conjugated α-mouse secondary antibody (no. A9044; Sigma-Aldrich) per standard procedures. Bands were illuminated by ECL-Plus Visualization System (GE Healthcare) and exposed to film per standard procedure and digitized. Protein expression was quantified by integration of the relevant band intensity with ImageJ software (National Institutes of Health [NIH], Bethesda Md.) and normalized to β-actin control.

miRNA Candidate Determination

The Sanger miRBase Targets v5 database was queried as described through the MicroCosm interface located online at http://microrna.sanger.ac.uk/. Briefly, this system uses the miRanda algorithm to determine and score sites of complementarity between mRNA 3' UTR sequences and known human miRNA species. Predicted interactions are favored that exhibit a high degree of complementarity at the 5' end of the miRNA, predicted thermodynamic stability by the Vienna RNA folding routines, and occur in UTR sequences conserved across multiple species.

Polymerase Chain Reaction and Luciferase Vector Construction

RNA was obtained from UCB MNC or isolated CD4$^+$ T cells with the PureLink Micro-to-Midi RNA Isolation kit (Invitrogen, Carlsbad, Calif.) and then DNase treated (DNA-free; Ambion, Austin, Tex.). After DNase removal, cDNA was generated from RNA as described below for reverse transcription-polymerase chain reaction (RT-PCR) and subjected to 30 rounds of PCR per standard protocol with the following primers to verify the presence of the predicted targeted sequence: 5'-TTACTATTTGGACGGAACACC-3' (reverse, both reactions) (SEQ ID NO:3), 5'-TATGAAACA-GAATGACTGTGATC-3' (forward, NM_012340 reaction) (SEQ ID NO:4), and 5'-CTACTTGGATGATGTTAAT-GAAAT-3' (forward, NM_173091 reaction) (SEQ ID NO:5). These PCRs additionally generated 3' UTR sequences containing the full-length intervening sequence between the stop codon and the predicted miR-184 interacting site. This sequence (NM_012340 reaction only) was cloned into the pMIR-Report plasmid at the 3' UTR position following the luciferase gene per the manufacturer's instructions (Ambion). In addition, short (38-mer) synthesized DNA sequences matching the plus and minus strand, including and surrounding the predicted targeted site were dimerized and cloned into the same vector. "Control" denotes pMIR-Report without either insert.

CD4$^+$ Cell Transfection

CD4$^+$ T cells were transfected with luciferase vectors, synthetic precursor miRNA (no. 17000/17010; Ambion), and/or antisense miRNA inhibitor (no. 17100/17110; Ambion) via Amaxa Nucleofector (Amaxa, Gaithersburg, Md.) per the manufacturer's protocol for unstimulated human T cells provided in the Human T-cell kit (no. VPA-1002) using program U-14. Approximately 1 μg plasmid or DNA sequence was transfected per 10$^6$ cells. Typical efficiencies in control green fluorescent protein (GFP) plasmid transfections were approximately 50%.

Luciferase Assay

Cells were transfected with the aforementioned constructs alongside a consistent quantity of pGL4.71 [hRlucP] plasmid (Promega, Madison, Wis.) to control for transfection efficiency. Cells were lysed and prepared per the manufacturer's instructions (Dual-Luciferase Reporter Assay System, no. E1910; Promega) and luciferase activity was measured via fluorescence on a NOVOStar plate reader (BMG Labtech, Durham, N.C.).

Quantitative RT-PCR cDNA was generated from whole cellular RNA by Multi-Scribe Reverse Transcriptase (Applied Biosystems, Foster City, Calif.) per the manufacturer's instructions. TaqMan RT-PCR assays were prepared per the manufacturer's instructions (Applied Biosystems) using probes for either NFATc2 (no. Hs00234855_m1) or IL2 (Hs00174114_m1). Endogenous control for all relative mRNA quantifications was glyceraldehyde 3-phosphate dehydrogenase (GAPDH; no. Hs99999905_m1), and reactions were run in at least triplicate per experiment. qRT-PCR was carried out on an Applied Biosystems 7500 thermal cycler per the manufacturer's instructions. Relative expression was quantified from the amplification curves using the 7500 Fast System Software. For relative mature miRNA quantification, small RNA was enriched with the Mission Small RNA Isolation kit (Sigma-Aldrich) and qRT-PCR carried out using the TaqMan miRNA Reverse Transcription kit (Applied Biosystems) and primers for hsa-miR-184 (no. 4373113) or U47 snoRNA control (no. 4380911) and run per manufacturer's instructions.

Statistical Analysis

Quantitative RT-PCR error bars represent SEM assuming a 95% confidence interval. Luciferase error bars represent sample SD of the representative experiment. Quantified Western blot analysis error bars represent SEM for the stated number of experiments, and P values were calculated by Student t test and 1-way analysis of variance (ANOVA).

Figure 2:
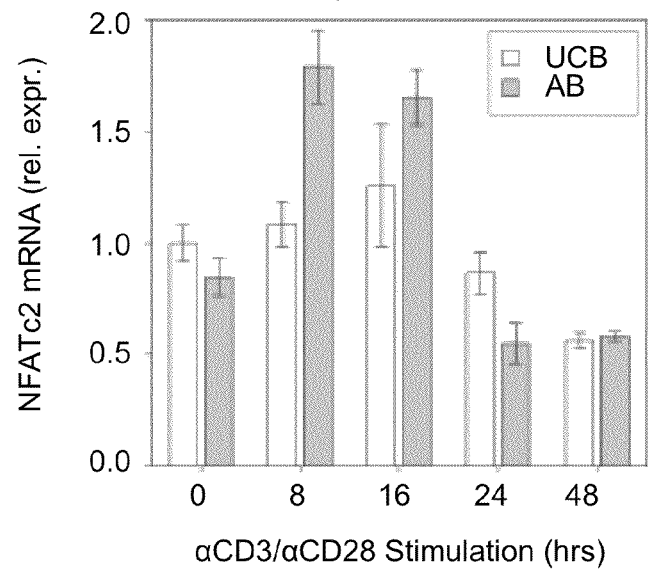
FIG. 2 illustrates a graph showing NFATc2 (NFAT1-encoding) mRNA expression in stimulated UCB and AB CD4+ T cells assayed by qRT-PCR as described and normalized to UCB at 0 hours.

UCB CD4$^+$ T Cells Express Significantly Less NFAT1 Protein but not mRNA Compared with AB CD4$^+$ T Cells To determine the nature of the mechanism underlying reduced NFAT1 protein expression in UCB CD4$^+$ T cells, an in vitro stimulation time course of UCB and AB CD4$^+$ T cells was performed, and expression of NFAT1 protein and its mRNA transcript were compared. Western blot analysis comparing NFAT1 protein expression in UCB CD4$^+$ T cells versus AB during primary stimulation confirmed reduced baseline expression and attenuated up-regulation in UCB. This discrepancy is evident throughout 48 hours of αCD3/αCD28 stimulation in vitro (FIG. 1). NFATc2 transcript levels from multiple donors were measured by qRT-PCR as described and compared between UCB and AB samples (FIG. 2). These findings reveal only modest differences in relative NFATc2 mRNA quantity, which are insufficient to account for the NFAT1 protein expression discrepancy in UCB versus AB CD4$^+$ T cells.

Due to the dramatic differences in protein expression without significant corresponding differences in mRNA quantity, potential mechanisms of NFAT1 posttranscriptional regulation were investigated. Through proteasome inhibition and cellular fractionation experiments, translocation of the NFATc2 mRNA into polysomes by UCB CD4$^+$ cells was observed to lag behind AB CD4$^+$ T cells by at least 6 hours during in vitro stimulation. Because similar effects have been observed in other confirmed miRNA/mRNA interactions and our previous microarray studies had failed to reveal significant differences in translational initiation or elongation factors, we focused our subsequent work on identifying potential miRNA species that could specifically affect the translation of NFAT1 in UCB CD4$^+$ T cells.

miR-184 is Predicted to Interact Strongly with the 3' UTR of the NFATc2 mRNA

A search to determine specific miRNAs that may contribute to the observed differences in UCB CD4$^+$ T-cell NFAT1 protein expression was conducted. Putative miRNA regulators were determined by querying the Sanger MicroCosm resource and miRBase targets registry. Many miRNA sequences predicted to bind to the 3' UTR of NFAT1 were identified by this computational analysis (highest scoring candidates shown in Table 1). Of the 58 and 35 predicted microRNA binders (for each transcript variant, National Center for Biotechnology Information [NCBI] accession nos. NM_012340 and NM_173091, respectively) identified by this query, the strongest predicted binder to the 3' UTR (both variants) was miR-184, a recently characterized miRNA present in a variety of tissues and suggested to be of importance in DNA methylation pathways and a potential antagonist of miR-205. Conversely, the strongest predicted mRNA target of miR-184 (based on a reciprocal analysis of the miRNA sequence) was the previously identified sequence within the NFAT1 3' UTR (Table 2). The NM_173091 variant lacks a 3' exon containing the NM_012340 stop codon, but both variants show full homology downstream of that region. The complementary miR-184/NFATc2 sequences are diagrammed in FIG. 3, with the predicted interaction occurring 399 and 299 nucleotides downstream of the stop codons, respectively.

TABLE 1

Table 1 Predicted NFATc2-interacting miRNAs

| Transcript variant (NCBI accession no., microRNA ID | Score | Energy | Base P | Start | End |
|---|---|---|---|---|---|
| NM_012340 | | | | | |
| has-miR-187 | 19.7351 | −29.74 | $6.81 \times 10^{-4}$ | 329 | 350 |
| has-miR-135a | 18.3064 | −14.69 | $7.16 \times 10^{-3}$ | 89 | 111 |
| has-miR-494 | 18.2857 | −14.34 | $8.75 \times 10^{-3}$ | 285 | 306 |
| has-miR-765 | 18.1568 | −25.71 | $2.32 \times 10^{-2}$ | 159 | 179 |
| has-miR-23a | 17.8397 | −26.38 | $2.06 \times 10^{-2}$ | 129 | 150 |
| has-miR-30b | 17.7282 | −23.31 | $3.38 \times 10^{-2}$ | 173 | 194 |
| has-miR-29c | 17.6167 | −17.7 | $1.05 \times 10^{-2}$ | 324 | 344 |
| has-miR-29a | 17.6167 | −17.64 | $1.01 \times 10^{-2}$ | 324 | 344 |
| has-miR-342-5p | 17.5964 | −20.89 | $1.27 \times 10^{-2}$ | 305 | 325 |
| has-miR-135b | 17.4188 | −13.41 | $1.57 \times 10^{-2}$ | 89 | 111 |
| has-miR-30c-1 | 17.2822 | −18.77 | $3.15 \times 10^{-2}$ | 173 | 194 |
| has-miR-30c-2 | 17.2822 | −17.22 | $2.72 \times 10^{-2}$ | 173 | 194 |
| has-miR-302b | 17.1707 | −9.66 | $1.71 \times 10^{-2}$ | 24 | 45 |
| has-miR-302d | 17.1707 | −13.13 | $1.34 \times 10^{-2}$ | 24 | 45 |
| has-miR-29b | 17.086 | −16.53 | $1.85 \times 10^{-2}$ | 323 | 344 |
| has-miR-29a | 17.0592 | −16.53 | $3.67 \times 10^{-2}$ | 74 | 95 |
| has-miR-21 | 17.036 | −14.3 | $1.45 \times 10^{-2}$ | 323 | 344 |
| has-miR-801 | 17.0057 | −26.53 | $1.09 \times 10^{-2}$ | 196 | 219 |
| NM_173091 | | | | | |
| has-miR-184 | 20.1255 | −25.74 | $4.53 \times 10^{-4}$ | 229 | 250 |
| has-miR-494 | 18.6473 | −14.34 | $6.44 \times 10^{-3}$ | 185 | 206 |
| has-miR-765 | 18.5179 | −25.71 | $1.69 \times 10^{-2}$ | 59 | 79 |
| has-miR-23a | 18.1925 | −26.38 | $1.51 \times 10^{-2}$ | 29 | 50 |
| has-miR-30b | 18.0788 | −23.31 | $2.43 \times 10^{-2}$ | 73 | 94 |
| has-miR-29c | 17.9651 | −17.7 | $7.70 \times 10^{-3}$ | 224 | 244 |
| has-miR-29a | 17.9651 | −17.64 | $7.41 \times 10^{-3}$ | 224 | 244 |
| has-miR-342-5p | 17.9463 | −20.89 | $8.91 \times 10^{-3}$ | 205 | 225 |
| has-miR-30c-2 | 17.624 | −17.22 | $1.91 \times 10^{-2}$ | 73 | 94 |
| has-miR-30c-1 | 17.624 | −18.77 | $2.22 \times 10^{-2}$ | 73 | 94 |
| has-miR-29b | 17.4222 | −16.53 | $1.37 \times 10^{-2}$ | 223 | 244 |
| has-miR-21 | 17.3748 | −14.3 | $1.06 \times 10^{-2}$ | 223 | 244 |
| has-miR-801 | 17.3388 | −26.53 | $7.57 \times 10^{-3}$ | 96 | 119 |
| has-miR-452 | 17.2829 | −13.26 | $1.75 \times 10^{-2}$ | 236 | 257 |
| has-miR-369-5p | 17.2829 | −17.61 | $2.56 \times 10^{-3}$ | 212 | 233 |
| has-miR-135a | 17.196 | −11.51 | $2.24 \times 10^{-2}$ | 1 | 11 |
| has-miR-330-5p | 17.1692 | −19.06 | $4.48 \times 10^{-2}$ | 195 | 217 | microRNAs predicted to interact with the 3' UTR of each NFATc transcript. The Sanger microRNA database was queried for the NFATc2 transcript asa described. (Last accessed Jul. 15, 2008.) Table reflects all miRNAs scoring higher than 17.0

TABLE 2

| mRNA | Score | P |
|---|---|---|
| NFATC2 | 20.1255 | $4.53 \times 10^{-4}$ |
| SMPDL3B | 19.557 | $8.20 \times 10^{-4}$ |
| GPBAR1 | 19.1021 | $1.05 \times 10^{-3}$ |
| LMO1 | 19.0877 | $1.34 \times 10^{-3}$ |
| MPL | 18.9884 | $1.48 \times 10^{-3}$ |
| PSMA4 | 18.6473 | $1.19 \times 10^{-4}$ |
| ABO | 18.5336 | $2.38 \times 10^{-3}$ |
| THOP1 | 18.3249 | $5.10 \times 10^{-5}$ |
| TPM3 | 18.1925 | $3.40 \times 10^{-3}$ |
| GAS6 | 18.1856 | $3.42 \times 10^{-3}$ |
| ANKRD54 | 18.1508 | $3.55 \times 10^{-3}$ |
| CXYorf3 | 18.1496 | $8.49 \times 10^{-4}$ |
| TCEAL4 | 18.0965 | $3.75 \times 10^{-3}$ |
| GAS6 | 18.0921 | $3.77 \times 10^{-3}$ |
| PZP | 18.0788 | $3.82 \times 10^{-3}$ |
| C20orf196 | 18.056 | $3.92 \times 10^{-3}$ |
| SIDT2 | 17.997 | $3.20 \times 10^{-5}$ |
| ZBED3 | 17.9705 | $4.28 \times 10^{-3}$ |
| FAM72B | 17.9651 | $4.30 \times 10^{-3}$ |
| TFF3 | 17.9651 | $6.29 \times 10^{-4}$ |

Genes predicted to interact with miR-184 in humans. The Sanger microRNA database was queried for human transcripts with predicted complementary to miR-184. (Last accessed Jul. 15, 2008.) Table reflects the top 20 results with duplicates removed.

miR-184 is more Highly Expressed in UCB than in AB CD4+ and Decreases through Early Stimulation Time Points The expression of miR-184 in unstimulated UCB CD4+ T cells was on average quantified 58.4 times higher than in AB CD4+ T cells by qRT-PCR (FIG. 4A). Notably, neonatal CD4+ T cells are known to contain a higher proportion of naive recent thymic emigrants than AB, although NFAT1 expression is lacking in both RA+ and RO+ subsets UCB and not expressed differently in either subset in AB. The expression of miR-184 was observed to be much more highly skewed toward the naive (CD45RA+) CD4+ subset in AB than in UCB.

The expression of miR-184 over a time course of in vitro simulation was also measured (FIG. 4B). Subjecting isolated and stimulated UCB CD4+ T cells to the same qRT-PCR assay at early time points revealed a modest decline in miR-184 quantity (40% of original by 6 hours). Later time points at which the eventual up-regulation of NFAT1 protein expression is observable in UCB, but still dramatically lower compared with AB (FIG. 1) exhibit an eventual rebound in miRNA expression by 16 hours and modest up-regulation through 48 hours. Conversely, detectable miR-184 expression in AB CD4+ cells is observed to drop dramatically over the same time points after stimulation (FIG. 4C).

mIR-184 Affects Protein Expression through its Predicted Binding Site on the NFATc2 mRNA To confirm the presence of the predicted binding site in the NFATc2 transcript, whole cell mRNA was isolated from UCB MNC and selected CD4+ T cells, transcribed into cDNA as described in the methods for qRT-PCR, and subjected to PCR using primers directed to sites adjacent to the stop codons and overlapping the 3' end of the predicted binding sequence (FIG. 5A). The gel bands verify the actual presence of the predicted target site within the 3' UTR of both transcript variants. Complete sequencing of the insertions within our generated luciferase vectors further confirms this observation.

To determine whether miR-184 indeed interacts with the corresponding NFATc2 sequence as predicted (FIG. 3), expression vectors designed to transcribe a luciferase-encoding mRNA containing either a short synthetically prepared sequence matching only the predicted miR-184 binding site from NFATc2 ("184-only") or the NFATc2 (NM_012340 variant) 3' UTR through and including the aforementioned sequence ("cloned UTR") were constructed. The full-length NFATc2 3' UTR has not been fully cloned or sequenced, and we wished to avoid the effects of any possible variations in UTR length between samples or cell types. These vectors were introduced into UCB (FIG. 5B) and AB (FIG. 5C) selected CD4+ T cells. Luciferase assays indicate only 38% and 60% expression compared with control when luciferase expression is influenced by the 184-only sequence and the cloned UTR, respectively (FIG. 5B). This effect is almost completely reversed when a blocking antisense sequence to miR-184 is cotransfected. However in AB, the 184-only insertion has no effect on luciferase activity (middle column, white bar), whereas insertion of the cloned UTR results in a 58% reduction in expression (FIG. 5C). Transfection of an exogenous precursor to miR-184 results in decreases of 61% and 23%, respectively (middle bars). This effect is again attenuated when a blocking antisense sequence is cotransfected with the miR-184 precursor (rightmost bars). These data indicate that miR-184 does indeed modulate protein expression through its predicted binding site and suggests significant endogenous miR-184 activity in UCB but not AB CD4+ T cells.

To further confirm these observations, we mutated the cloned UTR luciferase expression vector insert used previously to disrupt either the seed region (by removing the 4 3'-most nucleotides from its predicted binding site; "-seed region") or the entire predicted binding site ("-184 site"). Base pair binding within the seed region has been shown to often be of importance to translational repression by miRNA. We observed a 4- and 3-fold induction, respectively, of luciferase expression in UCB CD4+ cells when either the seed region or the miR-184 binding site was removed (FIG. 5D). However, we observed a comparatively slight (1.5-fold) increase in expression when the same vectors were transfected into AB CD4+ cells (FIG. 5E). Failure to observe a significant change in luciferase expression with inhibition of miR-184 activity in UCB or introduction of miR-184 in AB (gray bars) confirmed the specificity of the observed effect.

miR-184 Activity Directly Affects NFAT1 Protein Quantity in Unstimulated CD4+ T Cells To determine whether endogenous miR-184 can directly repress NFAT1 protein expression in UCB CD4+ T cells, Western blot analysis for NFAT1 was performed on unstimulated selected CD4+ T cells after transfection with either control or blocking antisense to miR-184 (FIG. 6A right). Band intensities were quantified and normalized to β-actin, and relative NFAT1 expression under the influence of each treatment was compared. Aggregate data (FIG. 6A left) reveal an 86% increase in NFAT1 protein expression when the cells were treated with antisense to miR-184. NFATc2 mRNA levels (FIG. 6B) were however unchanged between samples Likewise, when unstimulated AB CD4+ T cells are transfected with a synthesized precursor to miR-184 (FIG. 6C), NFAT1 protein levels as quantified by Western blot analysis are reduced by approximately 31%. However, interference with miR-184 in AB CD4+ cells failed to yield an observable change in NFAT1 protein expression (FIG. 6D). This series of experiments indicates negative regulation of NFAT1 protein through the microRNA pathway by miR-184 in UCB CD4+ T cells and further suggests a nondegrading mechanism of action.

miR-184 Activity Conversely Affects Production of the NFAT-Associated IL-2 Transcript To determine whether manipulation of NFAT1 protein levels through interference with the activity of miR-184 is sufficient to result in an increase in transcription of NFAT1-target genes, the transcription of IL-2, a gene strongly activated by NFAT1 binding to its promoter after stimulation, 14 was assayed by qRT-PCR. UCB CD4+ cells were transfected with blocking antisense to miR-184, assayed for up-regulated NFAT1 expression by Western blot analysis (data included in FIG. 6A) after 16 hours, and then stimulated in vitro as described previously. Data reflect a significantly greater amount of IL-2 mRNA in the miR-184 antisense treated samples at 6 hours of stimulation. This increase is maintained through 16 hours (FIG. 7A). Conversely, AB CD4+ T cells transfected with an exogenous miR-184 precursor exhibited dramatically reduced IL-2 transcription through the same stimulation time points (FIG. 7B). These findings indicate that miR-184 interference with NFAT1 in UCB CD4+ T cells is indeed sufficient to influence both NFAT1 protein levels and transcription of the known NFAT1 target gene, IL2.

Our findings comprise the first observation of miR-184 activity in immune cells and a characterization of its activity on a key transcriptional regulator of inflammation specifically known to exhibit decreased activity in UCB CD4+ T cells. We identified miR-184 as a strong predicted regulator of NFAT1 and confirmed its interaction with the observed complementary binding site within the NFATc2 mRNA 3' UTR. UCB CD4+ T cells were shown to exhibit significantly more miR-184 RNA and miR-184-mediated repressive activity than AB CD4+ T cells. We additionally confirmed through blocking and gain-of-function analyses that manipulation of miR-184 is sufficient to influence NFAT1 protein as well as its known downstream target, IL-2.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

The invention claimed is:

1. A method of decreasing NFATc2 activity in a lymphocyte, comprising administering to the lymphocyte an amount of an NFATc2 mRNA antagonist that binds to a binding site on the 3'UTR of NFATc2 mRNA effective to decrease the activity of NFATc2 mRNA in the lymphocyte, the NFATc2 mRNA antagonist comprising microRNA having a nucleotide sequence substantially homologous to SEQ ID NO: 1.

2. The method of claim 1, wherein the lymphocyte is a CD4+ T cell.

3. The method of claim 2, wherein the CD4+ T cell is administered to the bone marrow of a subject.

4. The method of claim 3, wherein the CD4+ T cell is administered in a transplantable material.

5. The method of claim 3, wherein the CD4+ T cell is not endogenous to the subject.

6. The method of claim 5, wherein the CD4+ T cell has been transplanted into the subject.

7. A method of decreasing NFATc2 expression in a lymphocyte, comprising administering to the lymphocyte an amount of an NFATc2 mRNA antagonist effective to decrease the activity of NFATc2 mRNA in the lymphocyte, the NFATc2 antagonist comprising microRNA having nucleotide sequence substantially homologous to SEQ ID NO:1.

8. The method of claim 7, wherein the lymphocyte is a CD4+ T cell.

9. The method of claim 8, wherein the CD4+ T cell is administered to the bone marrow of a subject.

10. The method of claim 9, wherein the CD4+ T cell is administered in a transplantable material.

11. The method of claim 8, wherein the CD4+ T cell is not endogenous to the subject.

12. The method of claim 8, wherein the CD4+ T cell has been transplanted into the subject.

13. A method of preventing or reducing immune incompatibility in a subject, the method comprising administering to the subject or tissue transplanted to the subject a therapeutically effective amount of an NFATc2 antagonist, the NFATc2 antagonist comprising microRNA having nucleotide sequence substantially homologous to SEQ ID NO:1.

14. The method of claim 13, wherein the subject has or is at risk for having graft versus host disease.

15. The method of claim 13, wherein the subject has or is at risk for having graft rejection.

16. The method of claim 13, wherein the subject is the recipient of a transplant.

17. The method of claim 13, wherein the subject is the recipient of a hematopoietic stem cell transplant.

* * * * *

SEQUENCE LISTING

<160> NUMBER OF SEQ ID NOS: 5

<210> SEQ ID NO 1
<211> LENGTH: 22
<212> TYPE: RNA
<213> ORGANISM: Homo sapiens

<400> SEQUENCE: 1
uggacggaga acugauaagg gu                                          22

```
<210> SEQ ID NO 2
<211> LENGTH: 43
<212> TYPE: RNA
<213> ORGANISM: Homo sapiens

<400> SEQUENCE: 2
auccugguug aucuuaaugg uguuccgucc aaauaguaaa uag          43

<210> SEQ ID NO 3
<211> LENGTH: 21
<212> TYPE: DNA
<213> ORGANISM: Homo sapiens

<400> SEQUENCE: 3
ttactatttg gacggaacac c                                  21

<210> SEQ ID NO 4
<211> LENGTH: 23
<212> TYPE: DNA
<213> ORGANISM: Homo sapiens

<400> SEQUENCE: 4
tatgaaacag aatgactgtg atc                                23

<210> SEQ ID NO 5
<211> LENGTH: 24
<212> TYPE: DNA
<213> ORGANISM: Homo sapiens

<400> SEQUENCE: 5
ctacttggat gatgttaatg aaat                               24
```